United States Patent
Maxson et al.

(10) Patent No.: US 9,138,259 B2
(45) Date of Patent: Sep. 22, 2015

(54) EXTERNAL TIBIAL MILL GUIDE AND METHOD OF USE

(71) Applicant: Biomet Sports Medicine, LLC, Warsaw, IN (US)

(72) Inventors: William Maxson, Fort Wayne, IN (US); Brian K. Berelsman, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 420 days.

(21) Appl. No.: 13/720,659

(22) Filed: Dec. 19, 2012

(65) Prior Publication Data

US 2014/0171952 A1    Jun. 19, 2014

(51) Int. Cl.
A61B 17/16    (2006.01)
A61B 17/17    (2006.01)
A61B 17/56    (2006.01)
A61B 17/15    (2006.01)

(52) U.S. Cl.
CPC .............. *A61B 17/56* (2013.01); *A61B 17/157* (2013.01); *A61B 17/16* (2013.01); *A61B 17/1615* (2013.01); *A61B 17/1662* (2013.01); *A61B 17/1675* (2013.01); *A61B 17/17* (2013.01); *A61B 17/1739* (2013.01); *A61B 17/1764* (2013.01); *A61B 2017/1602* (2013.01); *A61B 2017/564* (2013.01)

(58) Field of Classification Search
CPC .......... A61B 17/16; A61B 2017/1602; A61B 17/1615; A61B 17/1662; A61B 17/1675; A61B 17/17; A61B 17/1739; A61B 17/1764; A61B 17/56; A61B 2017/564
See application file for complete search history.

(56) References Cited

U.S. PATENT DOCUMENTS

| | | | |
|---|---|---|---|
| 4,516,277 A | 5/1985 | Butel | |
| 4,718,907 A | 1/1988 | Karwoski et al. | |
| 4,775,426 A | 10/1988 | Murley et al. | |
| 5,228,459 A | 7/1993 | Caspari et al. | |
| 5,486,180 A | 1/1996 | Dietz et al. | |
| 5,908,424 A | 6/1999 | Bertin et al. | |
| 6,025,536 A | 2/2000 | Bender et al. | |
| 6,576,104 B1 | 6/2003 | Nasu et al. | |
| 6,969,393 B2 | 11/2005 | Pinczewski et al. | |
| 7,608,079 B1 * | 10/2009 | Blackwell et al. | 606/87 |
| 7,867,236 B2 | 1/2011 | Hodorek et al. | |
| 8,021,368 B2 | 9/2011 | Haines | |
| 2005/0192588 A1 * | 9/2005 | Garcia | 606/88 |
| 2007/0055269 A1 * | 3/2007 | Iannarone et al. | 606/87 |
| 2010/0305711 A1 | 12/2010 | McKinnon et al. | |
| 2010/0331847 A1 | 12/2010 | Wilkinson et al. | |
| 2010/0331991 A1 | 12/2010 | Wilkinson et al. | |
| 2011/0130762 A1 | 6/2011 | Metzger et al. | |
| 2011/0208256 A1 | 8/2011 | Zuhars | |
| 2012/0078254 A1 | 3/2012 | Ashby et al. | |

* cited by examiner

*Primary Examiner* — Larry E Waggle, Jr.
(74) *Attorney, Agent, or Firm* — Schwegman Lundberg & Woessner, P.A.

(57) ABSTRACT

A cutting guide includes a jig assembly that is configured to attach to a second surface of a bone. The jig assembly includes a guide block that defines a jig recess and that is configured to be disposed adjacent to the first surface. Also, the cutting guide includes a tool support that is moveably coupled to the jig assembly, and the tool support is configured to couple to the cutting tool and moveably support the cutting tool on the jig assembly. Moreover, the cutting guide includes an adapter that is removably received within the jig recess to adapt a dimension of the jig recess according to a corresponding dimension of the pocket. The adapter includes at least one adapter surface that is configured to abut the guide portion of the cutting tool to thereby limit movement of the cutting portion relative to the first surface of the bone.

24 Claims, 8 Drawing Sheets

EXTERNAL TIBIAL MILL GUIDE AND METHOD OF USE

FIELD

The present disclosure relates to a tibial mill guide and, more particularly, to an external tibial mill guide and a method of using the same.

BACKGROUND

This section provides background information related to the present disclosure which is not necessarily prior art.

Anatomical joints, such as knee joints, can become damaged due to age, injury, etc., causing pain and/or loss of mobility of the joint. Therefore, various prosthetic joints have been proposed for restoring the joint. These prosthetic joints can include a first component that fixes to the first bone of the joint and a second component that fixes to the second bone of the joint. A bearing can also be included between the first and second prosthetic components.

In preparation for implantation of a prosthetic device, the bones are typically resected or otherwise prepared such that the bone surface can mate securely with the prosthetic device. Various cutting guides have been proposed for guiding a cutting tool during this procedure. Use of cutting guides can ensure that the surface of the bone is prepared in a controlled manner.

SUMMARY

This section provides a general summary of the disclosure, and is not a comprehensive disclosure of its full scope or all of its features.

A cutting guide for guiding cutting of a pocket within a first surface of a bone by a cutting tool is disclosed. The bone also includes a second surface that is spaced away from the first surface. The cutting tool includes a cutting portion and a guide portion. The cutting guide includes a jig assembly that is configured to attach to the second surface of the bone, and the jig assembly includes a guide block that is configured to be disposed adjacent to the first surface. The guide block defines a jig recess. Also, the cutting guide includes a tool support that is moveably coupled to the jig assembly, and the tool support is configured to couple to the cutting tool and moveably support the cutting tool on the jig assembly. Moreover, the cutting guide includes an adapter that is removably received within the jig recess to adapt a dimension of the jig recess according to a corresponding dimension of the pocket. The adapter includes at least one adapter surface that is configured to abut the guide portion of the cutting tool to thereby limit movement of the cutting portion relative to the first surface of the bone.

A method of forming a pocket within a first surface of a bone using a cutting tool is disclosed. The bone also includes a second surface that is spaced away from the first surface. The cutting tool includes a cutting portion and a guide portion. The method includes determining a pocket dimension of the pocket and attaching a jig assembly with a guide block that defines a jig recess to the second surface of the bone. The method also includes selecting an adapter according to the determined pocket dimension. Moreover, the method includes removably positioning the selected adapter within the jig recess to adapt a dimension of the jig recess according to the determined pocket dimension. Furthermore, the method includes coupling the cutting tool to a tool support of the jig assembly. Additionally, the method includes moving the cutting tool and the tool support relative to the jig assembly and the adapter while the cutting tool is coupled to the tool support such that the cutting portion cuts the pocket in the first surface. Furthermore, the method includes abutting the guide portion against an adapter surface of the adapter to limit movement of the cutting portion relative to the first surface of the bone according to the determined pocket dimension.

In addition, a cutting guide for guiding cutting of a pocket within a superior surface of a tibia by a cutting tool is disclosed. The tibia also includes an anterior surface. The cutting tool includes a cutting portion and a guide portion. The cutting guide includes a jig assembly including an attachment body and a guide block. The attachment body is configured to fixedly attach to the anterior surface of the tibia, and the guide block is moveably supported by the attachment body and configured to be disposed adjacent to the superior surface. The guide block defines a jig recess. The cutting guide additionally includes a tool support that is moveably coupled for substantially linear movement in a first direction on the jig assembly. The tool support is configured to couple to the cutting tool and moveably support the cutting tool on the jig assembly. The tool support is configured to slidingly receive the cutting tool for sliding movement of the cutting tool relative to the tool support in a second direction. The second direction is substantially perpendicular to the first direction. Moreover, the cutting guide includes an adapter that is removably received within the jig recess to adapt a width dimension and a transverse dimension of the jig recess according to corresponding dimensions of the pocket. The adapter includes at least one adapter surface that is configured to abut the guide portion of the cutting tool to thereby limit movement of the cutting portion relative to the superior surface of the tibia.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

Figure 1:
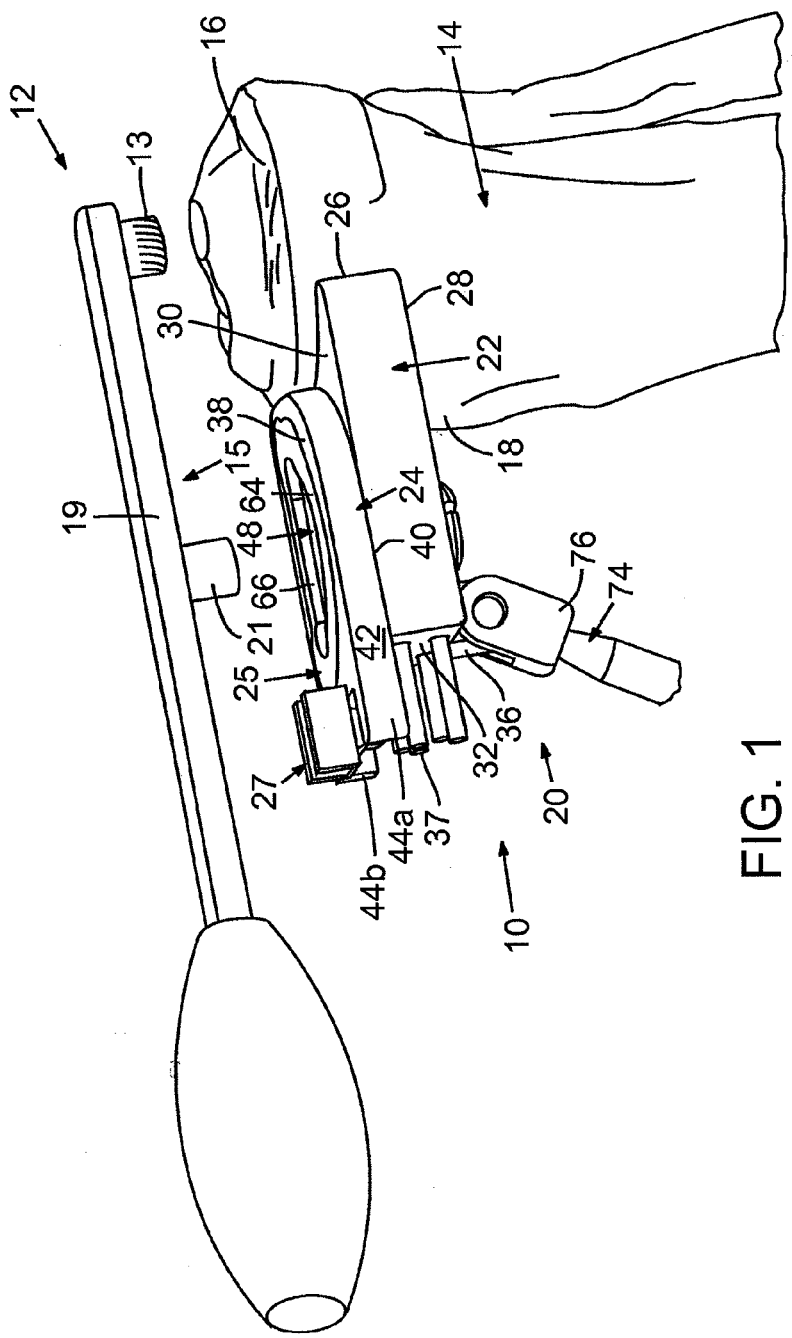
FIG. 1 is a perspective view of a cutting guide and a cutting tool according to various embodiments of the present disclosure.
Figure 9:
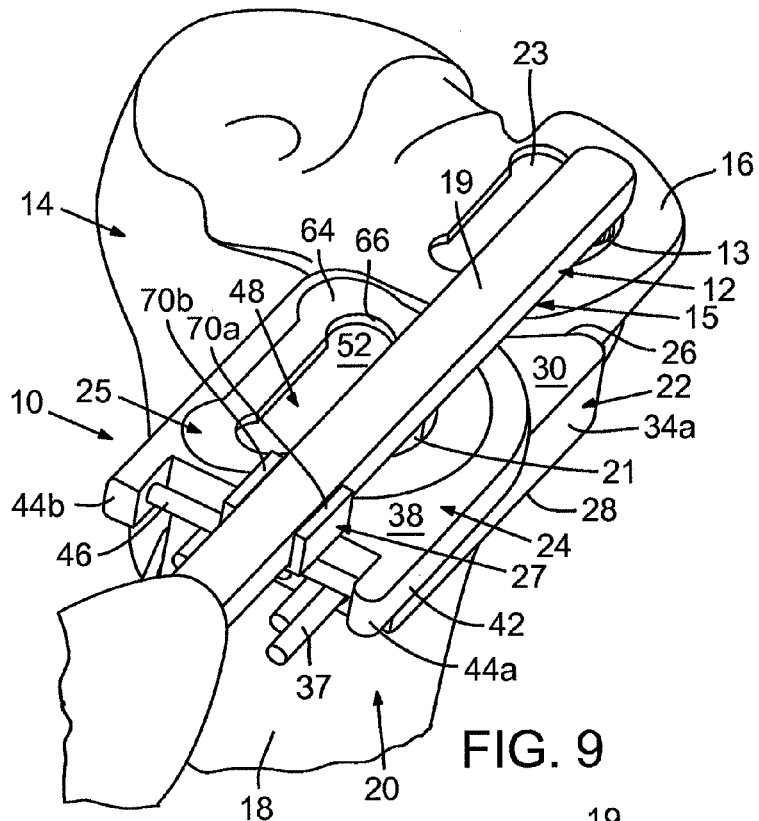
FIG. 9 is a perspective view of the cutting tool being used in combination with the cutting guide of FIG. 1.
Figure 10:
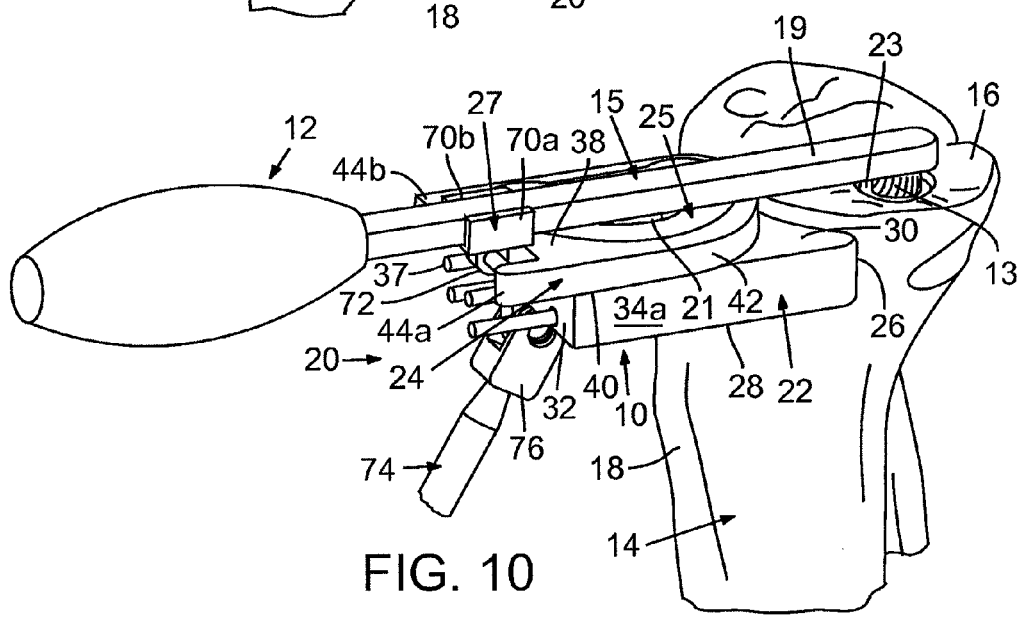
FIG. 10 is a perspective view of the cutting tool being used in combination with the cutting guide of FIG. 1.

Referring initially to FIGS. 1, 9, and 10, a cutting guide 10 is illustrated according to exemplary embodiments of the present disclosure. The cutting guide 10 can be used for guiding a cutting tool 12 when cutting a pocket 23 (FIGS. 9 and 10) within a bone, such as a tibia 14 or other bone. As shown in the embodiments illustrated, the guide 10 can be used for guiding the cutting tool 12 relative to a superior surface 16 (i.e., a first surface) of the tibia 14 so that the pocket 23 (FIGS. 9 and 10) can be formed in a controlled manner on the superior surface 16. However, it will be appreciated that the cutting guide 10 can be used for guiding movement of the cutting tool 12 toward any surface of the tibia 14 or any other bone.

It will also be appreciated that the pocket 23 can be prepared to receive a prosthetic device, such as an inlay implant (e.g., a REPICCI™ implant, which is commercially available from Biomet, Inc. of Warsaw, Ind.). Furthermore, it will be appreciated that the term "pocket" is defined herein to include a wide variety of recesses, openings, holes, etc. These pockets can have any suitable size and shape (e.g., can be sized and shaped according to the size, shape, etc. of the prosthetic implant to be implanted therein). Additionally, although the guide 10 is shown and described as being used for formation of a pocket 23 on the medial articular surface of the tibia 14, it will be appreciated that the guide 10 could be configured for formation of a pocket 23 in the lateral articular surface. Still further, it will be appreciated that the cutting guide 10 can be used for repairing the joint during an arthroscopic or during a so-called open surgical procedure.

The cutting tool 12 can include a cutting portion 13, which can be of any suitable type for cutting bone, tissue, etc. For instance, the cutting portion 13 can be cylindrical and can include sharpened cutting edges, fluting, etc., similar to a burr-type tool. The cutting portion 13 can also be mounted for rotation on the tool 12, similar to a mill bit. Accordingly, the cutting portion 13 can form the pocket 23 in the tibia 14 as will be discussed. The cutting tool 12 can also include a guide portion 15, which abuts portions of the cutting guide 10 such that the cutting guide 10 guides formation of the pocket 23 as will be discussed in detail below. For instance, in the embodiments illustrated, the guide portion 15 of the cutting tool 12 can include an elongate arm 19 that has a relatively straight axis. The cutting portion 13 can extend perpendicularly from one end of the arm 19. The guide portion 15 can further include a post 21, which can be cylindrical and can have a shape and size corresponding to that of the cutting portion 13. The post 21 can also extend perpendicularly from the arm 19 and can be parallel to and spaced from the cutting portion 13. During formation of the pocket 23 in the tibia 14, the post 21 and/or the arm 19 can abut corresponding surfaces of the cutting guide 10 while the cutting portion 13 penetrates and cuts into the tibia 14. Thus, abutment between the guide portion 15 of the cutting tool 12 and the cutting guide 10 can limit movement of the cutting portion 13 relative to the superior surface 16 of the tibia 14. As such, the size of the pocket 23 can be controlled. More specifically, the depth of the pocket 23 in the distal direction can be controlled, the transverse size of the pocket 23 in the anterior/posterior direction can be controlled, and/or the transverse size of the pocket 23 in the medial/lateral direction can be controlled in various embodiments.

Figure 2:
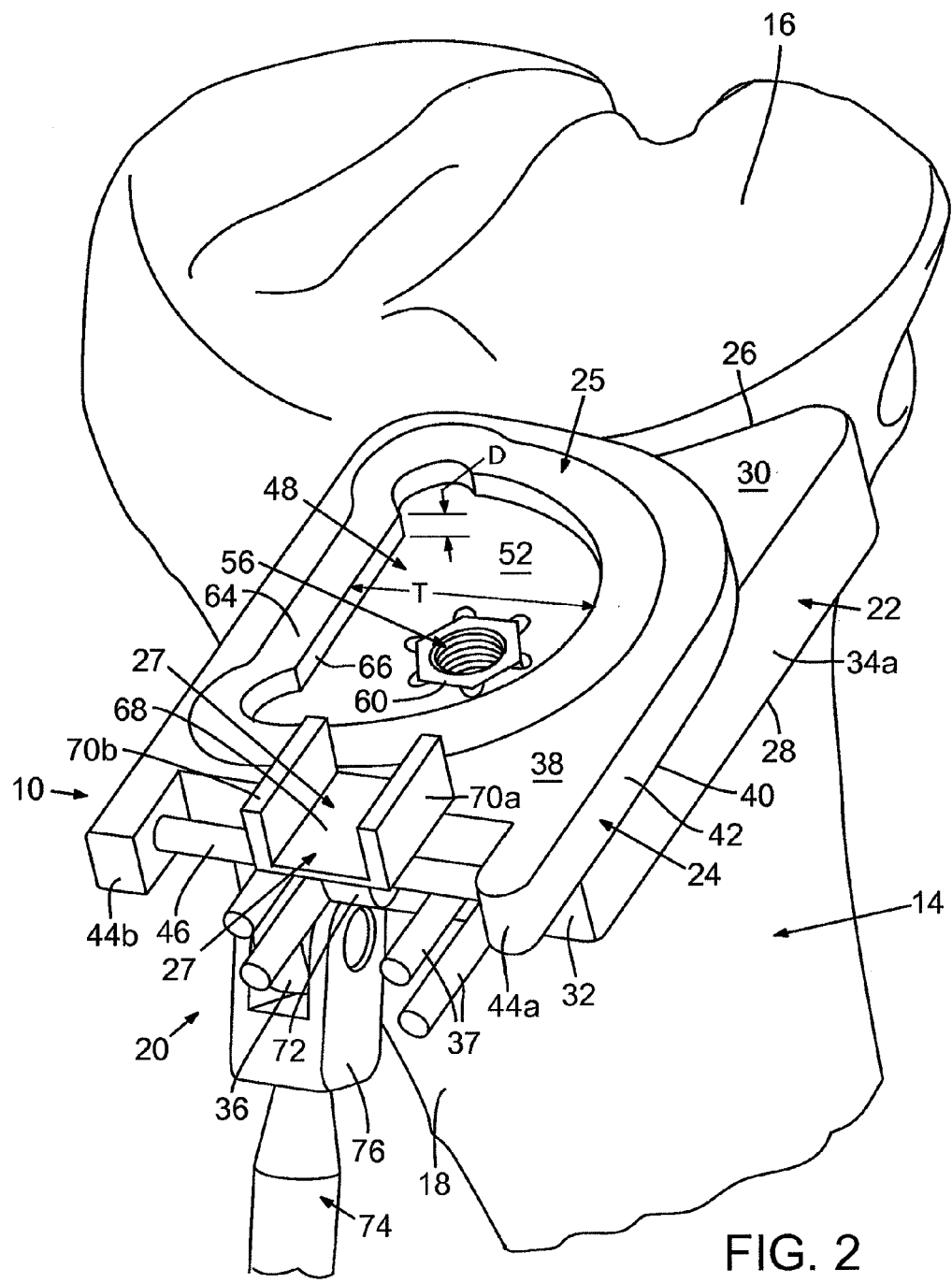
FIG. 2 is a perspective view of the cutting guide of FIG. 1.
Figure 3:
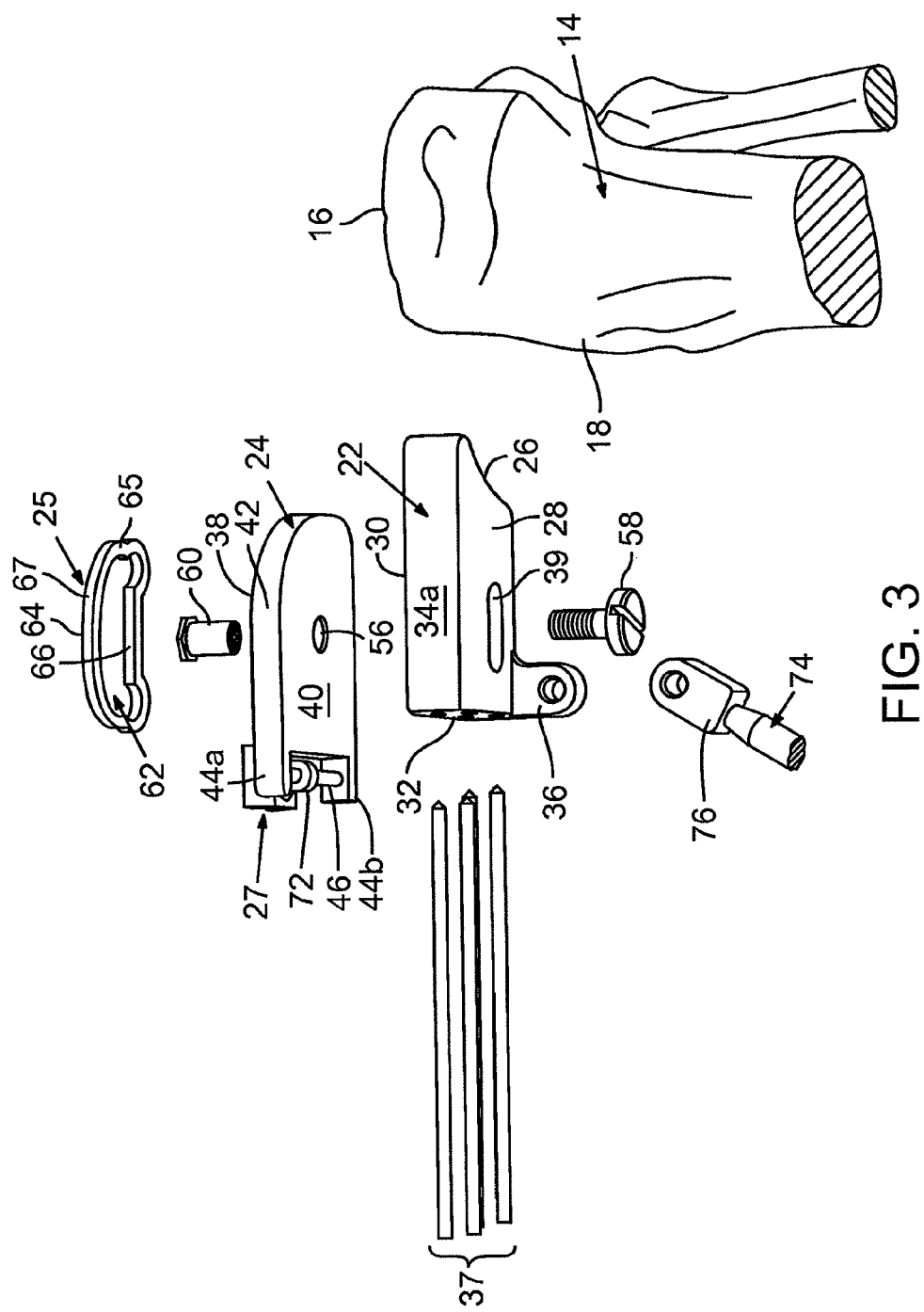
FIG. 3 is an exploded perspective view of the cutting guide of FIG. 1.

As shown in FIGS. 1-3, the cutting guide 10 can generally include a jig assembly 20, an adapter 25, and a tool support 27. Each of these components will now be discussed in detail.

Figure 4:
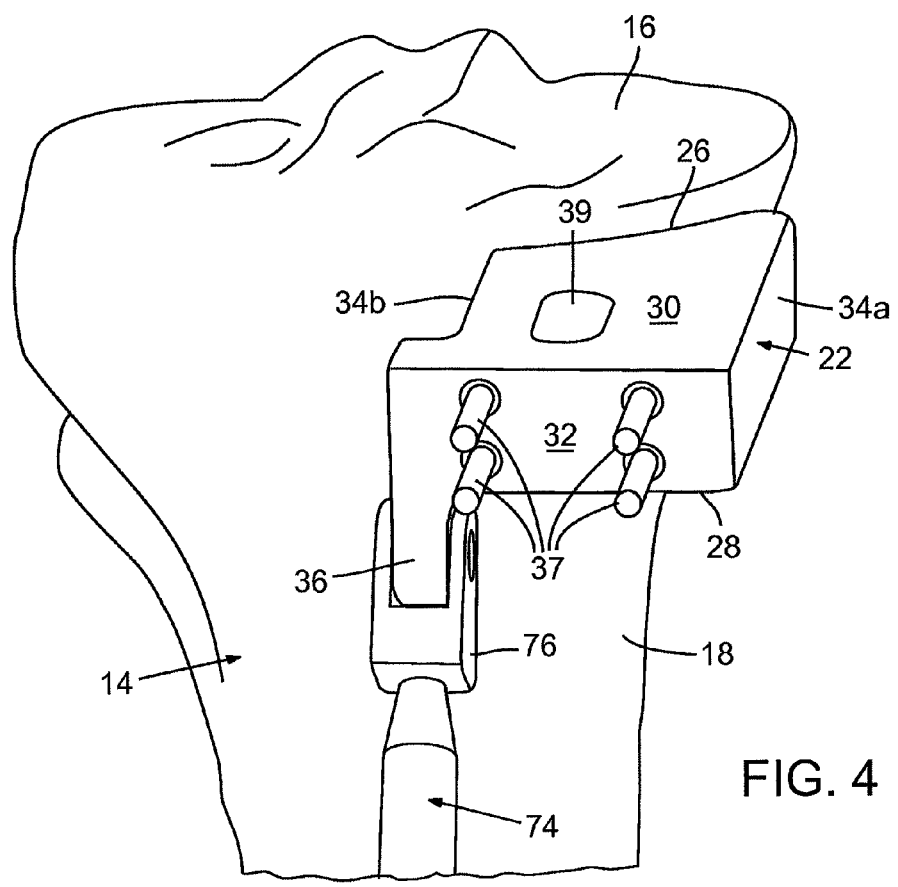
FIG. 4 is a perspective view of an attachment body and an alignment rod of the cutting guide of FIG. 1.

The jig assembly 20 can include an attachment body 22 that is most clearly viewed, for instance, in FIGS. 3 and 4. The attachment body 22 can be block shaped and can be made from a rigid material, such as stainless steel, etc. The attachment body 22 can include a back surface 26 (i.e., an engaging surface), which can be curved in two or three dimensions so as to generally conform to the shape of the tibia 14 and/or any surrounding tissue. For instance, the back surface 26 can be curved so as to generally conform to the shape of the anterior surface 18 (i.e., second surface) of the tibia 14. This curvature can be generally configured to use with several different patients, or the curvature of the back surface 26 could be patient-specific (e.g., can be a curved so as to closely nest against a particular patient's tibia 14).

The attachment body 22 can further include a bottom surface 28 and a top surface 30, which can be flat, and which can extend substantially perpendicularly from the back surface 26. Moreover, the attachment body 22 can include a front surface 32, which can be flat and can extend substantially perpendicularly between the bottom and top surfaces 28, 30. The attachment body 22 can additionally include side surfaces 34a, 34b, which can be flat and can extend perpendicularly between the bottom and top surfaces 28, 30 and between the front and back surfaces 26, 32. Additionally, the attachment body 22 can include a flat, partially rounded projection 36, which projects inferiorly from the bottom surface 28, adjacent the intersection of the side surface 34b and the front surface 32. Moreover, the attachment body 22 can include a slot 39 that extends longitudinally through the top and bottom surfaces 28, 30. The slot 39 can include a major axis that extends substantially perpendicular to the front surface 32.

The attachment body 22 can be removably fixed to the anterior surface 18 of the tibia 14 via a plurality of pins 37. The pins 37 can extend perpendicularly through the front surface 32 and can extend out through the back surface 26 to penetrate into the tibia 14. It will be appreciated that the attachment body 22 could couple to the tibia 14 using other fasteners or other means as well.

Figure 5:
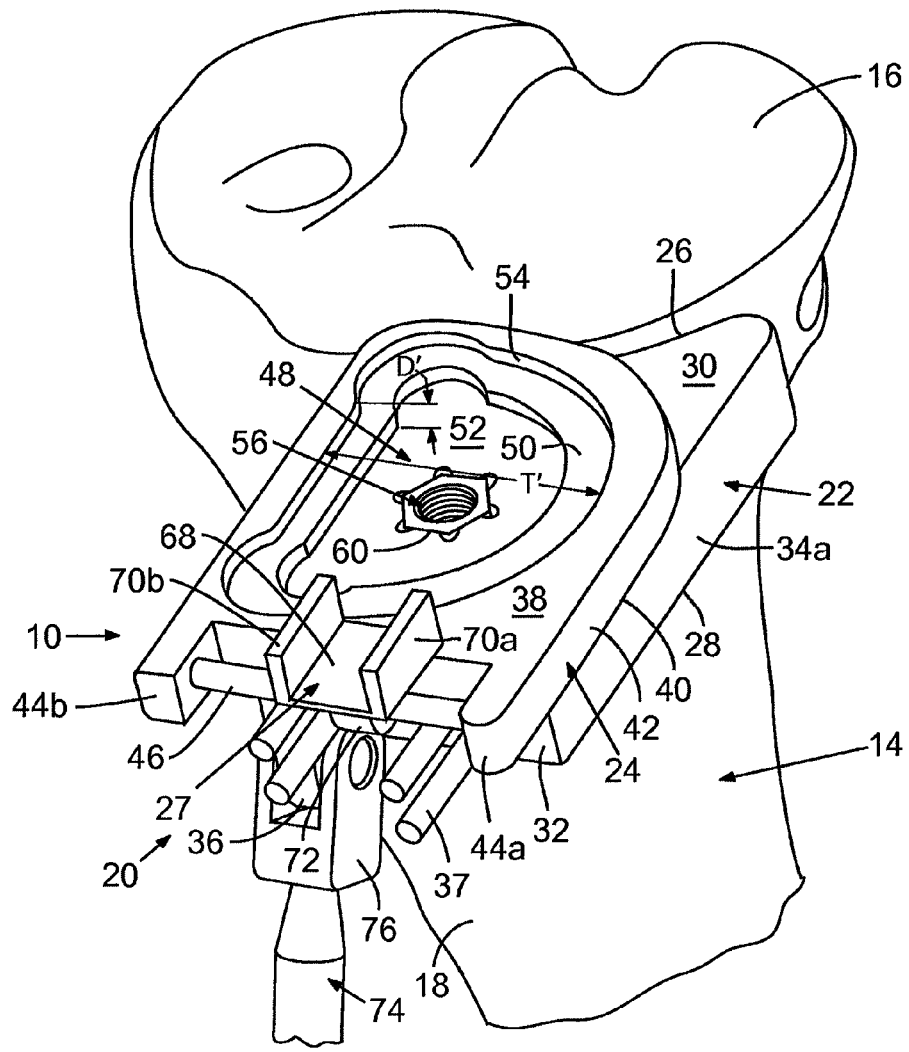
FIG. 5 is a perspective view of the cutting guide of FIG. 1, wherein an adapter is removed.
Figure 6:
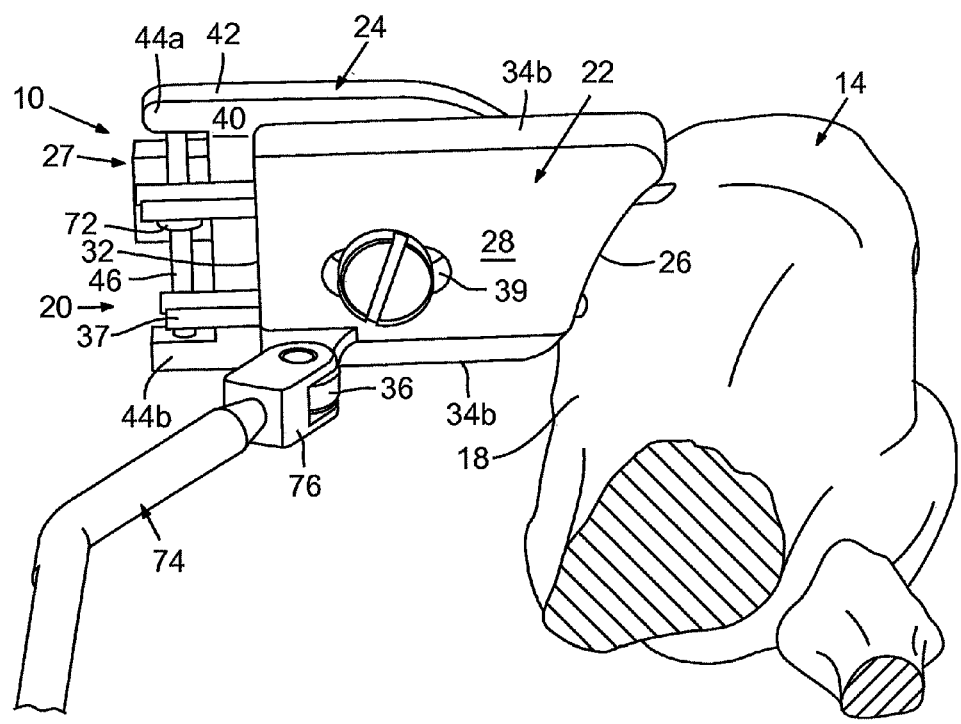
FIG. 6 is a superiorly directed perspective view of the cutting guide of FIG. 1.

The jig assembly 20 can further include a guide block 24, which is most clearly illustrated in FIGS. 3, 5, and 6. The guide block 24 can include a top surface 38, a bottom surface 40, and a side surface 42. The bottom surface 40 can be substantially flat and can be slidably supported atop the top surface 30 of the attachment body 22. The side surface 42 can be curved and can extend perpendicularly from the bottom surface 40. The top surface 38 can include a recess 48 (i.e., a jig recess). In some embodiments, the recess 48 can be generally D-shaped and can define at least one step 50 therein. Thus, the recess 48 can include a bottom surface 52 (FIG. 5), which is substantially parallel to the bottom surface 40 of the guide block 24, and the recess 48 can include a side surface 54, which extends substantially perpendicularly to the bottom surface 52 of the recess 48. Accordingly, it will be appreciated that the recess 48 can define a depth dimension D", which is measured perpendicular to the bottom surface 52 from the bottom surface 52 to the top surface 38 as shown in FIG. 5. Also, the recess 48 can define a transverse dimension T", which can be measured parallel to the bottom surface 52 in the medial/lateral direction, the anterior/posterior direction, etc.

Moreover, the guide block 24 can include a plurality of (e.g., two) projections 44a, 44b, which are relatively thin and that project from the side surface 42. When the guide block 24 is supported atop the attachment body 22, the projections 44a, 44b can project from the front surface 32 of the attachment body 22 in the anterior direction. A rod 46 can be fixed at both ends to the projections 44a, 44b. The rod 46 can be axially straight.

Moreover, the guide block 24 can include a through hole 56 that extends through the top and bottom surfaces 38, 40. As shown in FIGS. 3, 5, and 6, a bolt 58 and nut 60 can be received in the hole 56 and the slot 39 of the attachment body 22. In some embodiments, the nut 60 can be recessed below the bottom surface 52 of the jig recess 48, and the nut 60 can have a smaller diameter than the post 21 of the cutting tool 12. The bolt 58 and nut 60 can be threadably attached together. When the bolt 58 and nut 60 are tightened down, the guide block 24 and attachment body 22 can be fixed together, and when loosened, the guide block 24 can rotate relative to the attachment body 22 about the axis of the hole 56. It will be appreciated that the cutting guide 10 could include another retaining device other than the bolt 58 and nut 60 (e.g., a clamp, another type of fastener, etc.) for selectively retaining the guide block 24 relative to the attachment body 22. Thus, as will be discussed, the guide block 24 can be rotated relative to the attachment body 22 during assembly of the cutting guide 10, during sizing of the tibia 14, etc. Then, when the guide block 24 is in a desired position, the bolt 58 and nut 60 can be tightened to selectively retain the guide block 24 in position relative to the attachment body 22.

The cutting guide 10 can additionally include an adapter 25 as shown in FIGS. 2, 3, 9, and 10. The adapter 25 can have a shape that corresponds to the jig recess 48 such that the adapter 25 can nest therein. Thus, in the embodiments shown, the adapter 25 can be D-shaped and can include a top surface 64, a bottom surface 65, an interior surface 66, an exterior surface 67, and a through hole 62 that extends between the top and bottom surfaces 64, 65 (see FIG. 3). The bottom surface 65 can be stepped so as to correspond to the step 50 of the jig recess 48 in some embodiments. The adapter 25 can be removably received within the jig recess 48 such that the bottom surfaces 65, 52 lie against each other and the exterior surface 67 of the adapter 25 lies against the side surface 54 of the jig recess 48. Also, in this position, the through hole 62 of the adapter 25 can partially expose the bottom surface 52 of the jig recess 48. Accordingly, the adapter 25 can adapt the size (i.e., change the dimensions) of the jig recess 48.

For instance, the jig recess 48 without the adapter 25 (FIG. 5) can have a transverse dimension (e.g., width) T' that is greater than a comparable dimension T of the jig recess 48 with the adapter 25 inserted therein (FIG. 2). The depth dimension D' of the recess 48 without the adapter 25 can be the same as the depth dimension D of the recess 48 with the adapter 25 inserted therein, or in additional embodiments, the adapter 25 can change the depth of the recess 48. It will be appreciated that the adapter 25 can alter the dimensions of the jig recess 48 in any suitable fashion. As will be discussed, the adapter 25 can change the jig recess 48 according to the patient's anatomy such that the cutting guide 10 can be customized for the patient, etc.

In some embodiments, there can be a group of adapters 25, and each can be separately received in the jig recess 48; however, each adapter 25 can change the dimensions of the jig recess 48 differently. For instance, each adapter 25 in the group can have a different width (e.g., measured between the interior and exterior surfaces 66, 67 of the respective adapter 25), and/or a different height (e.g., measured between the top and bottom surfaces 64, 65 of the respective adapter 25). Thus, as will be discussed, the surgeon can select an adapter 25 that adapts the dimensions of the jig recess 48 in a desired fashion.

As mentioned, the cutting guide 10 can include the tool support 27 (FIGS. 1, 2, 5, 6, 8, 9, and 10), which can moveably support the cutting tool 12 on the jig assembly 20. In some embodiments, the tool support 27 can include a bottom wall 68 and plural (e.g., two) side walls 70a, 70b that extend transversely (e.g., perpendicularly) from the bottom wall 68, away from the jig assembly 20. Moreover, the tool support 27 can include a projection 72 that slideably receives the rod 46 of the guide block 24. Thus, the tool support 27 can slide along the axis of the rod 46 relative to the guide block 24.

The size, shape, surface curvature, etc. of the tool support 27 can be configured according to corresponding surfaces of the guide portion 15 of the cutting tool. For instance, the bottom wall 68 and side walls 70a, 70b can be configured to receive and removably attach with the arm 19 of the cutting tool 12. Thus, the cutting tool 12 and the tool support 27 can move as a unit along the axis of the rod 46 of the guide block 24 (e.g., in the medial/lateral direction). Also, in some embodiments, the arm 19 can be slideably coupled to the tool support 27 for sliding movement in at least one other direction or axis (e.g., in the anterior/posterior direction). Stated differently, the tool support 27 and cutting tool 12 can be movable along at least one linear axis within a Cartesian coordinate system relative to the jig assembly 20 and the tibia 14 (e.g., moveable along the medial/lateral direction), and the tool support 27 can be constrained against movement along another axis within the Cartesian coordinate system (e.g., constrained against movement in the superior/inferior and anterior/posterior directions). However, the tool support 27 can slidably support the cutting tool 12 for movement along one of these axes (e.g., slidable along the anterior/posterior directions). Accordingly, the cutting tool 12 can be moveably supported atop the guide block 24, and the cutting tool 12 can cut the pocket 23 in a controlled manner as will be discussed in detail below.

In addition, the cutting guide 10 can include and/or can be used with an alignment rod 74. The alignment rod 74 can be elongate and rigid and can lie substantially within a single plane. The alignment rod 74 can include a superior end 76 that is pivotally coupled to the projection 36 (FIGS. 1-3), for instance, via a pin or other fastener. The rod 74 can further include an inferior end (not specifically shown). In some embodiments, the rod 74 can be a telescoping rod such that the longitudinal length of the rod 74 can be selectively adjusted, for instance, according to the length of the tibia 14. As will be discussed in detail below, the alignment rod 74 can be aligned with an axis of the tibia 14 to thereby align the attachment body 22 to the axis of the tibia 14.

Figure 7:
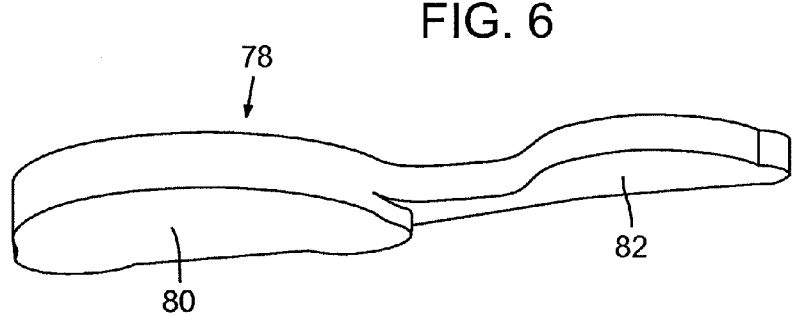
FIG. 7 is a perspective view of a sizer for use in combination with the cutting guide of FIG. 1.
Figure 8:
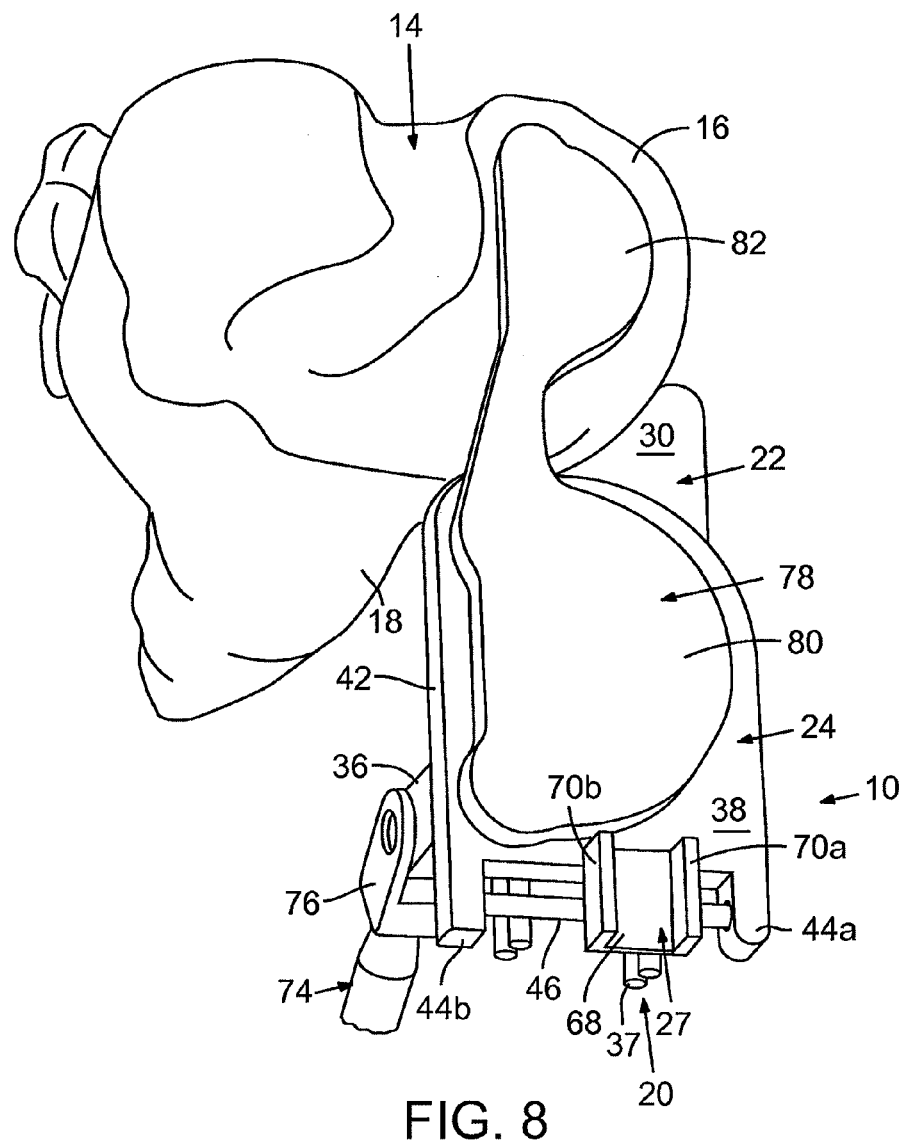
FIG. 8 is an inferiorly directed perspective view of the sizer of FIG. 7 shown coupled to the cutting guide of FIG. 1.

Additionally, as shown in FIG. 7, the cutting guide 10 can include an/or can be used with a sizer 78, which can be used for determining a size, shape, or other feature of the patient's tibia 14. The sizer 78 can be relatively flat and somewhat elongate and can include a coupling portion 80 and a sizing portion 82. The coupling portion 80 can be generally D-shaped and sized so as to be removably and securely received within the jig recess 48 (without the adapter 25). The sizing portion 82 can extend from the coupling portion 80 and can also be generally D-shaped in some embodiments. The area of the sizing portion 82 can correspond to the area of the pocket 23 to be formed in the tibia 14. As shown in FIG. 8, when the coupling portion 80 is received in the jig recess 48, the sizing portion 82 can overlap the superior surface 16 of the tibia 14. Accordingly, the sizing portion 82 can be compared to the superior surface 16 of the tibia 14 for intraoperatively determining a proper transverse dimension T of the pocket 23 (FIG. 2) as will be discussed in detail. In some embodiments, there can be a group of sizers 78, each having substantially the same coupling portion 80 but differently sized sizing portion 82. Thus, as will be discussed, the surgeon can choose between different sizers 78 for determining the proper size of the pocket 23 as will be discussed. Also, in some embodiments, the sizing portions 82 of the sizers 78 can correspond to different available adapters 25. For instance, the interior surface 66 of each adapter 25 can define a transverse dimension (e.g., width, length, etc.) that corresponds to that of at least one sizing portion 82 of the group of sizers 78.

To use the cutting guide 10, an incision can be made in the patient's skin (e.g., on the anterior of the patient's body, near the tibia 14). Then, the alignment rod 74 can be aligned with the axis of the tibia 14 (e.g., by aligning the rod 74 with the approximate center of the ankle and the approximate center of the superior surface 16 of the tibia 14), which can consequently align the attachment body 22 with the tibial axis. The position of the attachment body 22 relative to the tibia 14 in the superior/inferior direction can be determined by the surgeon according to measurements of the tibia 14, based on the surgeon's expertise, and/or other factors. Then, the attachment body 22 can be pinned or otherwise attached to the anterior surface 18 of the tibia 14 as shown in FIG. 4. The guide block 24 can be moveably coupled atop the attachment body 22 when the attachment body 22 is attached to the tibia 14, or the guide block 24 can be subsequently attached. In some embodiments, the guide block 24 can remain loosely attached to the attachment body 22 via the nut and bolt 58, 60 until the guide block 24 is positioned as desired relative to the tibia 14. Thereafter, the nut and bolt 58, 60 can be tightened to secure the guide block 24 in place.

Next, the surgeon can determine the size of the patient's tibia 14 and the proper size of the prosthetic device to implant therein. From this information, the surgeon can determine how big to make the pocket 23 in the tibia 14 so that the pocket 23 can securely receive the desired prosthetic device. Specifically, the coupling portion 80 of a sizer 78 can be removably received in the jig recess 48, and as such, the sizing portion 82 can overlap the superior surface 16 of the tibia 14 such that the sizing portion 82 can be compared with the superior surface 16 (FIG. 8). If the surgeon believes that the size (e.g., area, width, length, etc.) of the pocket 23 should be formed similar to that of the sizing portion 82, then the surgeon can choose the adapter 25 that corresponds with the sizer 78 being used. However, a different sizer 78 can be selected if the pocket 23 needs to be larger or smaller. Once the proper sizer 78 is identified and a corresponding adapter 25 is chosen, then the sizer 78 can be removed from the guide block 24, and the selected adapter 25 can be removably received within the jig recess 48.

Subsequently, the pocket 23 can be formed using the cutting tool as shown in FIGS. 9 and 10. The cutting portion 13 can rotate relative to the arm 19, and the arm 19 can be received within the tool support 27 such that the post 21 is received within the jig recess 48. This can occur while the cutting portion 13 cuts into the superior surface 16 of the tibia 14. The surgeon can move the tool support 27 (and, thus, the cutting tool 12) along the axis of the rod 46 (i.e., in the medial/lateral direction), and the surgeon can also slide the cutting tool 12 substantially perpendicular to this direction (i.e., in the anterior/posterior direction) relative to the tool support 27 while the cutting portion 13 cuts the pocket 23. The surgeon can also move the cutting tool 12 in the inferior direction to make the pocket deeper 23 until the arm 19 abuts the bottom wall 68 of the tool support 27.

It will be appreciated that the post 21 can abut the interior surfaces 66 of the adapter 25 to thereby limit the transverse dimensions of the pocket 23 (i.e., the interior surfaces 66 can be first adapter surfaces that limit transverse dimensions of the pocket 23). Also, in some embodiments, the arm 19 can abut the top surface 64 of the adapter 25 to thereby limit the depth of the pocket 23, and/or the post 21 can abut the bottom surface 52 of the jig recess 48 to thereby limit the depth of the pocket 23. (Stated differently, the top surface 64 of the adapter 25 or the bottom surface 52 can be second adapter surfaces that limit the depth of the pocket 23.) Once the pocket 23 is formed according to the adapted size of the jig recess 48, the cutting guide 10 can be removed from the tibia 14, and a prosthetic implant can be installed therein.

As such, the pocket 23 can be formed in a convenient and controlled manner. Accordingly, the resultant prosthetic joint can be implanted and assembled accurately. Thus, the knee joint can restore mobility to the joint, can reduce pain, and the like.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A cutting guide for guiding cutting of a pocket within a first surface of a bone by a cutting tool, the bone also including a second surface that is spaced away from the first surface, the cutting tool including a cutting portion and a guide portion, the cutting guide comprising:
    a jig assembly configured to attach to the second surface of the bone, the jig assembly including a guide block that is configured to be disposed adjacent to the first surface, the guide block defining a jig recess;
    a tool support that is moveably coupled to the jig assembly, the tool support configured to couple to the cutting tool and moveably support the cutting tool on the jig assembly; and
    an adapter that is removably received within the jig recess to adapt a dimension of the jig recess according to a corresponding dimension of the pocket, the adapter including at least one adapter surface that is configured to abut the guide portion of the cutting tool to thereby limit movement of the cutting portion relative to the first surface of the bone.

2. The cutting guide of claim 1, wherein the second surface is an anterior surface of a tibia, and the first surface is a superior surface of the tibia, the jig assembly being configured to attach to the anterior surface of the tibia.

3. The cutting guide of claim 1, wherein the adapter is generally D-shaped and includes a through hole.

4. The cutting guide of claim 1, wherein the pocket has a depth dimension and a transverse dimension, wherein the adapter includes a first adapter surface configured to limit movement of the cutting portion according to the transverse dimension of the pocket.

5. The cutting guide of claim 1, wherein the pocket has a depth dimension and a transverse dimension, wherein the adapter includes a second adapter surface configured to limit movement of the cutting portion according to the depth dimension of the pocket.

6. The cutting guide of claim 1, wherein the tool support is moveable within a Cartesian coordinate system relative to the jig assembly, and wherein the tool support is constrained against movement along at least one linear axis within the Cartesian coordinate system and is moveably coupled to the jig assembly along at least one other linear axis within the Cartesian coordinate system.

7. The cutting guide of claim 6, wherein the tool support is moveable along a first linear axis of the Cartesian coordinate system, and the tool support is configured to slidably support the cutting tool for movement along a second linear axis of the Cartesian coordinate system, the first and second linear axes being perpendicular to each other.

8. The cutting guide of claim 1, wherein the jig assembly includes an attachment body that is configured to removably attach to the second surface of the bone, wherein the guide block is moveably attached to the attachment body.

9. The cutting guide of claim 8, wherein the guide block is rotatably attached to the attachment body.

10. The cutting guide of claim 8, further comprising a retaining device that is configured to selectively fix the guide block relative to the attachment body.

11. The cutting guide of claim 1, further comprising an alignment rod that is coupled to the jig assembly, the alignment rod configured to align with a bone axis of the bone to thereby orient the guide block relative to the bone axis.

12. The cutting guide of claim 1, further comprising a sizer with a coupling portion and a sizing portion, the coupling portion being received within the jig recess to thereby locate the sizing portion over the first surface of the bone such that relative sizes of the first surface and the sizing portion are comparable.

13. The cutting guide of claim 1, further comprising the cutting tool.

14. A method of forming a pocket within a first surface of a bone using a cutting tool, the bone also including a second surface that is spaced away from the first surface, the cutting tool including a cutting portion and a guide portion, the method comprising:
determining a pocket dimension of the pocket;
attaching a jig assembly with a guide block that defines a jig recess to the second surface of the bone;
selecting an adapter according to the determined pocket dimension;
removably positioning the selected adapter within the jig recess to adapt a dimension of the jig recess according to the determined pocket dimension;
coupling the cutting tool to a tool support of the jig assembly;
moving the cutting tool and the tool support relative to the jig assembly and the adapter while the cutting tool is coupled to the tool support such that the cutting portion cuts the pocket in the first surface; and
abutting the guide portion against an adapter surface of the adapter to limit movement of the cutting portion relative to the first surface of the bone according to the determined pocket dimension.

15. The method of claim 14, wherein determining the pocket dimension includes coupling a coupling portion of a sizer to the jig assembly to thereby locate a sizing portion of the sizer over the first surface of the bone, and further comprising comparing relative sizes of the first surface and the sizing portion.

16. The method of claim 15, wherein coupling the cutting tool to the tool support results in the guide portion of the cutting tool being received in the jig recess.

17. The method of claim 14, wherein moving the cutting tool and the tool support relative to the jig assembly includes cooperatively moving the cutting tool and the tool support within a Cartesian coordinate system relative to the jig assembly, and wherein the tool support is constrained against movement along at least one linear axis within the Cartesian coordinate system.

18. The method of claim 17, wherein moving the cutting tool and the tool support relative to the jig assembly includes cooperatively moving the cutting tool and the tool support along a first linear axis of the Cartesian coordinate system, and sliding the cutting tool relative to the tool support along a second linear axis of the Cartesian coordinate system, the first and second linear axes being perpendicular to each other.

19. The method of claim 14, wherein attaching the jig assembly to the second surface of the bone includes attaching the jig assembly to an anterior surface of a tibia, wherein the first surface is a superior surface of the tibia.

20. The method of claim 14, wherein the pocket has a depth dimension and a transverse dimension, and wherein moving the cutting tool and the tool support relative to the jig assembly includes abutting a first adapter surface of the adapter and the guide portion to limit movement of the cutting portion according to the transverse dimension of the pocket.

21. The method of claim 14, wherein the pocket has a depth dimension and a transverse dimension, and wherein moving the cutting tool and the tool support relative to the jig assembly includes abutting a second adapter surface and the guide portion to limit movement of the cutting portion according to the depth dimension of the pocket.

22. The method of claim 14, further comprising moving the guide block relative to an attachment body of the jig assembly while the attachment body is removably attached to the second surface of the bone.

23. The method of claim 14, further comprising aligning an alignment rod with a bone axis of the bone to thereby orient the guide block relative to the bone axis.

24. A cutting guide for guiding cutting of a pocket within a superior surface of a tibia by a cutting tool, the tibia also including an anterior surface, the cutting tool including a cutting portion and a guide portion, the cutting guide comprising:
a jig assembly including an attachment body and a guide block, the attachment body configured to fixedly attach to the anterior surface of the tibia, the guide block moveably supported by the attachment body and configured to be disposed adjacent to the superior surface, the guide block defining a jig recess;
a tool support that is moveably coupled for substantially linear movement in a first direction on the jig assembly, the tool support configured to couple to the cutting tool and moveably support the cutting tool on the jig assembly, the tool support configured to slidingly receive the cutting tool for sliding movement of the cutting tool relative to the tool support in a second direction, the second direction being substantially perpendicular to the first direction; and
an adapter that is removably received within the jig recess to adapt a width dimension and a transverse dimension of the jig recess according to corresponding dimensions of the pocket, the adapter including at least one adapter surface that is configured to abut the guide portion of the cutting tool to thereby limit movement of the cutting portion relative to the superior surface of the tibia.

* * * * *